United States Patent [19]

Marx et al.

[11] 4,044,020
[45] Aug. 23, 1977

[54] PROCESS FOR PREPARING BIOTIN

[75] Inventors: Michael Marx, Sunnyvale, Calif.;
Josef H. Reisdorff, Wuppertal, Germany

[73] Assignee: Syntex (U.S.A.) Inc., Palo Alto, Calif.

[21] Appl. No.: 591,597

[22] Filed: June 30, 1975

[51] Int. Cl.$^2$ .......................................... C07D 495/04
[52] U.S. Cl. ............................ 548/303; 260/307 G; 260/332.2 H; 260/481 R
[58] Field of Search ...................................... 260/309.7

[56] References Cited
U.S. PATENT DOCUMENTS 2,417,326  3/1947  Schnider et al. .................. 260/309.7
2,437,719  3/1948  Wolf et al. ........................ 260/309.7

Primary Examiner—Natalie Trousof
Attorney, Agent, or Firm—Tom M. Moran; William B. Walker

[57] ABSTRACT

Biotin is prepared by (a) ozonizing methylcyclohexene; (b) reacting nitromethane with the methyl-6-oxohexanoate from a to form 7-nitro-6 hydroxyheptanoic acid methyl ester; (c) acylating to form the corresponding 6 acyloxy compound; (d) forming a double bond at the 6 position; (e) reacting the product of d with nitroethanethiol to form dl-7-thia-6-nitromethyl-9-nitro-nonanoic acid methyl ester; (f) forming a furoxan by cyclization; (g) reducing the furoxan and acylating to form dl-2(4-carbomethoxybutyl)-3,4-bis(acylamido)-2,5-dihydro thiophene; (h) selectively hydrogenating to form the 3,4-cis-bis(acylamido)-2,5-dihydro thiophene; and (i) hydrolyzing and cyclizing to form dl-biotin. The products formed at steps (e)–(h) are novel, as are the individual steps (e), (f), (g), and (h).

3 Claims, No Drawings

PROCESS FOR PREPARING BIOTIN

BACKGROUND OF THE INVENTION

1. Field of the Invention

This invention relates to a unique total synthesis for preparing dl biotin which starts with methoxycyclohexene and utilizes the basic concept of forming a furoxan system to construct the biotin nucleus. Within the total synthesis of biotin are several unique individual steps heretofore unknown in the prior art, as well as several unique intermediates which are formed in the process for making biotin.

2. Prior Art

Biotin is one of the water soluble vitamins which is a monocarboxylic acid containing a cylic urea structure with a sulfur in a thioether linkage as shown in FIG. 1 below

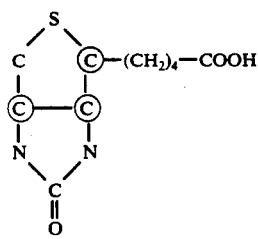

Biotin contains 3 asymmetric carbons (circled, above) and therefore there can exist as 4 racemates or 8 stereo isomers of the biotin structure. As a member of the vitamin B family biotin has, for a long time, been also known as the essential factor in the processes and maintenance of normal metabolism. Biotin's roles are discussed in an article entitled "Biotin-A Ubiquitous And Versatile Vitamin" by Dr. J. C. Bauernfeind, Feed Stuffs, 41, 32-34, 1969.

Several processes are known for preparing biotin and these are discussed in *Comprehensive Biochemistry*, 11, 66-81, Chapter VI entitled "Biotin" by L. H. Sternbach. As pointed out in that discussion, biotin was first synthesized by Harris and co-workers in the early 40's by forming a thiophene intermediate and eventually forming the keto 3,4 imidazolido group as the last step. A second route started with thiophane and proceeded through a series of reactions finally forming the 3,4 imidazolido group at the end of the reaction. A third synthesis also started with a substituted thiophane and progressed in a way similar to the second synthesis, however at each step meticulous care was taken to establish the steric configuration of the substituents in positions 3 and 4.

The commercial synthesis of biotin was developed by Hoffman La Roche and differs from the first three syntheses in several respects, i.a. that the imidazolidone ring is formed first with the 2 constituents (carbonyls) cis to each other.

The process for the synthesis of biotin according to this invention is a complete departure from anything taught in the prior art and involves starting with an alkoxy cyclohexane and proceeding through various steps to form a novel thieno furoxan structure and novel thiophenes to ultimately form biotin.

SUMMARY OF THE INVENTION

The process for preparing biotin by the process of this invention is set forth in the following reaction scheme

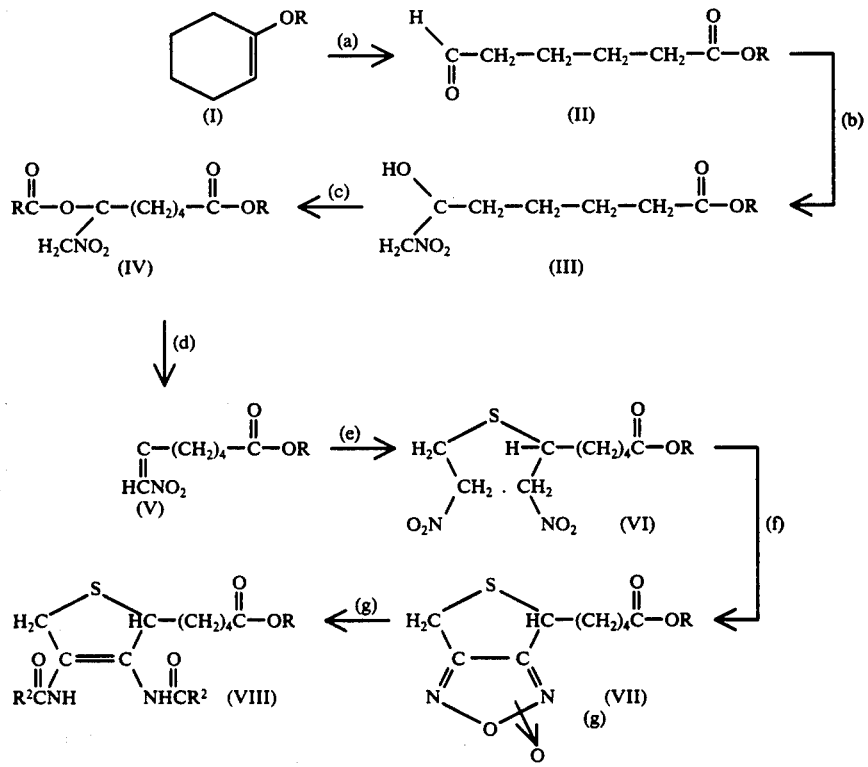

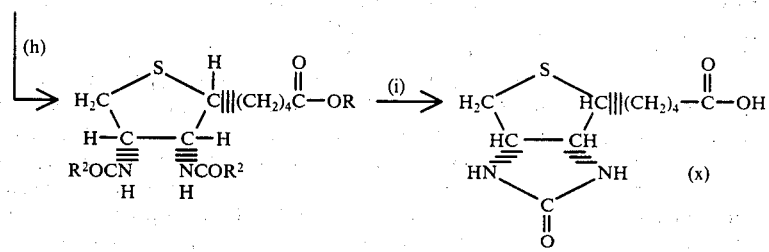

wherein R and R¹ may be alkyl of 1–4 carbons and R² is alkyl of 1–4 carbons which may be substituted with from 0–3 halogens. Steps e, f, g, h and i are novel per se while compounds VI, VII, VIII, and IX are also novel.

PREFERRED EMBODIMENTS

The process of this invention is broadly described in the following terms a. forming a lower alkyl-6-oxohexanoate by ozonization of a lower alkoxycyclohexene;

b. forming a lower alkyl ester of 7-nitro-6-hydroxy-heptanoic acid by reacting nitromethane with the alkyl-6-oxohexanoate from step a;

c. forming a lower alkyl ester of 7-nitro-6-acyloxyheptanoic acid by reacting the product from step b with an acylating agent;

d. forming a lower alkyl ester of 7-nitro-hept-6-enoic acid;

e. forming a lower alkyl ester of dl-7-thia-6-nitromethyl-9-nitro-nonanoic acid by the addition of nitroethanethiol at position 6 of the reaction product from step d above;

f. forming dl-6(4-carboalkoxy-butyl)-4H-6H-thieno-[3,4-d]furoxan by the appropriate cyclization reaction;

g. forming dl-2(4-carboalkoxy-butyl)-3,4-bis(alkamido)-2,5-dihydro-thiophene by reduction of the furoxan ring and reaction with an appropriate acylating agent;

h. forming dl-cis-2(4-carboalkoxy-butyl)-3,4-cis-bis (alkamido)-tetrahydrothiophene by selective hydrogenation;

i. forming dl-biotin by appropriate hydrolysis and cyclization reactions; and j. optionally resolving dl-biotin to d-biotin.

Each of the individual process steps will be discussed in a more complete manner hereafter pointing out the importance of each step as well as the novelty of the steps or the intermediate products where applicable. It is to be understood that this total synthesis is an entirely novel approach to the preparation of biotin and it is not intended to limit the manner in which each of the compounds are formed in each of the steps. Any method may be used which is suitable for the particular intermediate.

In the following discussion the Roman numerals refer to the structures so indicated in the previous reaction scheme.

a. Formation of lower alkyl ester of 6-oxohexanoic acid

The starting point for the overall synthesis of biotin by the process of this invention is a lower alkoxy cyclohexene (I) which may be obtained from any supply house which carries the substance or it may be prepared according to the process described by D. G. Lidsay, TET, 21, 1673 (1965). By lower alkyl is meant an aliphatic hydrocarbon containing 1 to 4 carbons and exemplified by methyl, ethyl, propyl, isopropyl, butyl, tertiary butyl, and the like. Preferably the starting material is methoxycyclohexene and this material shall be referred to hereafter as illustrative but not limiting.

The first step involves ozonizing the double bond of the cyclohexene ring to sever the ring and add oxo components at the previously joined carbons. The structure obtained is shown as II in the reaction scheme previously set forth. The methoxycyclohexene is treated with ozone in a suitable solvent under conditions sufficient to give the desired product. Generally these conditions will be a low temperature, that is less than $-50°$ C but no lower than about $-150°$ C. Preferably the temperature will be between about $-75°$ and $-80°$ C.

Any solvent which is substantially inert to the ozone at the temperatures employed may be used for this reaction. Because of its availability and cheapness, methanol is particularly preferred. Generally about 1 part by weight of methoxycyclohexene will be dissolved in about 5 to 15 parts by volume of the solvent. In the case of methanol a suitable ratio is about 1 part by weight to 10 parts by volume of the solvent.

The reaction generally takes place merely by placing the reactant and the solvent in a suitable container, cooling to the temperature desired, then bubbling ozone through the stirred solution for a time sufficient for the reaction to take place. Generally this time period is no more than an hour and preferably will be less than about 30 minutes. Excess ozone is removed from the reaction solution by an appropriate means which may simply involve bubbling nitrogen through the reaction solution.

It is thought that an intermediate ozonide may be formed prior to the complete severence of the cyclohexene ring. To ultimately form the desired 6-oxohexanoate the ozonide is treated, e.g. with a suitable amount of dimethylsulfide at the reaction temperature for a short period of time, for example less than an hour and preferably less than 15 minutes, whereafter the solution is allowed to come to ambient temperature while constantly stirring. This completes the reaction and hastens the formation of the 6-oxohexanoate. Excess solvent is then removed by means known in the art such as using a rotary evaporator. The reaction product, the methyl ester of 6-oxohexanoic acid may then be separated from the reaction mixture by any means known in the art sufficient to attain such separation, for example distillation.

b. Formation of lower alkyl ester of 7-nitro-6-hydroxy-heptanoic acid

In the next step the alkyl ester of 6-oxohexanoic acid from the previous step is reacted with nitromethane under basic conditions in a suitable solvent at low temperatures to form the lower alkyl ester of 7-nitro-6- hydroxy-heptanoic acid. Generally the solvent which may be employed is any solvent which is suitable for performing a nitromethylation and hydroxylation as is desired. Because of its effectiveness, availability and low cost methanol has been found to be particularly suitable and thus is preferred. Enough nitromethane and a suitable base such as a metal hydroxide is employed to provide the desired stoichiometric amount of the nitromethyl moiety. A suitable base may include metal hydroxides such as alkali or alkaline earth hydroxides such as the hydroxides of calcium, magnesium, sodium, potassium, and the like. Sodium hydroxide is particularly well suited for this purpose. Generally only a catalytic amount of base is necessary while a slight molar excess of nitromethane over the hexanoate will be used. The ratio of nitromethane to hexanoate will be about 1.1:1 to 2.0:1, preferably about 1.2:1 to 1.5:1.

Enough solvent is used to thoroughly dissolve the nitromethane and the hexanoate (II) as well as the base and to carry out the reaction effectively. For example, about 1 part by weight of the reactants will be dissolved in about 10 parts by volume to 20 parts by volume of the solvent. The reactants and the base are dissolved in the solvent and mixed together with vigorous stirring at a suitable temperature generally less than 10° C down to −50° C and preferably will be about −5° to +5° C. The reaction is carried on at low temperatures for less than an hour, preferably about 30 minutes then is allowed to warm up to ambient temperatures. Additional nitromethane may be added at this point to insure complete reaction. The reaction is allowed to go to completion at room temperature for a suitable period of time generally less than 24 hours and preferably will be less than about 12 hours. The resulting product is a mixture of the 2 stereo isomers of the methyl ester of 7-nitro-6-hydroxy-heptanoic acid, the 6 carbon atom being the asymmetric carbon. The product is recovered from the reaction mixture using suitable means of separation such as solvent removal by rotary evaporator and the mixture of isomers is then used for the next reaction step.

c. Forming the lower alkyl ester of 7-nitro-6-acyloxyheptanoic acid

The reaction product from the previous reaction step which includes the two stereo isomers, is reacted with a suitable acylating agent to add an acyloxy group at the 6 position of the heptanoic acid chain. The isomers from the previous step need not be separated since in the next step a double bond is formed which is opened at the subsequent step. A suitable acylating agent, such as a lower alkyl (1–4 carbons) acid or its halide or anhydride derivative may be any which are known in the art, but lower alkyl acid anhydrides (e.g. acetic anhydride) have been found to be particularly valuable. The crude mixture of isomers from step (b) may be taken up in e.g. acetic anhydride and the acetic anhydride is used not only as a solvent but also as a reactant. Generally about 1 part by weight of the isomer mixture will be dissolved in from 5 to 10 parts by volume of the anhydride. A small amount of a suitable acid catalyst such as concentrated sulfuric acid is added and the reactants are allowed to react in a stirred container at temperatures of about 10°–40° C, preferably about 25° C for a suitable length of time. Generally the length of time will be no more than 24 hours and preferably will be less than about 12 hours. The reaction yields the lower alkyl ester of 7-nitro-6-acyloxy-heptanoic acid which may be recovered from the reaction mixture by any suitable method, which includes removal of the excess anhydride at reduced pressure using a rotary evaporator. The resulting heptanoate is again a mixture of isomers which need not be separated before going on to the next step.

d. Formation of the lower alkyl ester of 7-nitro-hept-6-enoic acid

In the next step the product from the previous step is subjected to conditions which are suitable for an elimination reaction to take place and from a double bond between the 6 and the 7 position. Thus an acyloxy is eliminated and a hept-6-enoic acid is formed.

The elimination reaction will take place in a suitable solvent under basic conditions at slightly raised temperatures preferably in an inert atmosphere. A suitable solvent is found to be ethyl acetate, (although any functional equivalent may be acceptable) which is made slightly basic by the addition of a small amount of a suitable base, e.g. sodium bicarbonate, and a catalytic amount of water. Generally about 10 to 20 parts by volume of ethyl acetate will be used per one part by weight of the reactant and about a half part by weight of the sodium bicarbonate. A catalystic amount of water is that amount of water necessary to cause the reaction to go smoothly. Generally this will be no more than a few drops of water in the reaction mixture. The temperature at which the reaction may be run may be anywhere from 25° to 75° C and preferably will be about 40°–50° C for no more than about 5 hours, preferably less than 4 hours. After suitable recovery treatment the lower alkyl ester of 7-nitro-hept-6-enoic acid is obtained for the next step.

e. Formation of the lower alkyl ester of dl-7-thia-6-nitromethyl-9-nitro-nonanoic acid This step is carried out under conditions suitable for the nucleophilic addition of a nitroethanethio group at the 6 position of the lower alkyl ester of the 7-nitrohept-6-enoic acid. The reaction is carried out in a suitable solvent by dissolving both the nitroethanethiol and the reaction product from the previous step and stirring in an inert atmosphere for a suitable period of time at ambient temperatures. The reaction is substantially complete after less than 5 hours and preferably less than about 2 hours. A suitable solvent for this reaction may be any inert solvent useful for nucleophilic addition reactions, methanol being particularly effective. Methanol is used to about 1 to 10 parts by volume of methanol for each part by weight of nitroethanethiol.

f. Formation of dl-6(4-carbo lower alkoxy-butyl)-4H-6H-thieno [3,4-d]furoxan

This step involves the formation of the previously undescribed thieno [3,4-d] furoxan ring by a unique method heretofore unknown in the art. In this method the reaction product from the previous step, that is, the lower alkyl ester of dl-7-thia-6-nitromethyl-9-nitro-nonanoic acid, is placed in a suitable solvent and reactively contacted with a catalytic amount of a tertiary alkyl amine and phosphorus oxychloride (POCl$_3$) under substantially anhydrous conditions and in a substantially inert atmosphere. Suitable tertiary alkyl amine catalysts include triethyl amine, trimethyl amine, tributyl amine, tripropyl amine, and the like. Suitable solvents for this reaction are inert non-polar, aprotic solvents, e.g. halogenated hydrocarbons such as chloroform, the solvent being present in very large excess, for example about 10 to 1000 times the amount of the reactants used. The reaction is run at ambient temperatures, that is from about 10° C to about 40° C. Preferably at about 25° C. Preferably the tertiary alkyl amine catalyst and the phosphorus oxychloride are dissolved in the solvent and a solution of the product from the previous step in the solvent is added to the mixture. The reaction may take place over a period of anywhere from 10 to 24 hours but generally will take place within 18 hours. The resulting dl-6(4-carbo lower alkoxy-butyl)-4H-6H thieno[3,4-d]furoxan is a novel mixture, as well as each of the stereo isomers alone. Although furoxan rings are known to be prepared by the reaction of nitroethane and phenylisocyonate, see for instance JACS, 82, 5339–5342, Oct. 20, 1960 "The Reactions of Primary Nitro Paraffins With Nitro Isocyanates", Mukalyama & Hoshino, the preparation of the bicyclic intermediate of this invention in a single step from an acyclic precursor using phosphorus oxychloride and a tertiary amine catalyst is completely novel. The resulting furoxan compound is substantially stable and may be recovered from the reaction mixture using usual recovery techniques.

g. Formation of dl-2(4-carbo-lower alkoxy-butyl)-3,4-bis(alkamido)-2,5-dihydro thiophene The novel compound prepared in the previous step may then be converted into another novel compound heretofore unknown in the prior art by reducing the furoxan ring and reacting the resulting product with a suitable acylating agent. The furoxan ring may be reduced by catalytic hydrogenation or by using a suitable reducing reagent.

In the case of catalytic hydrogenation of the furoxan system, ordinary temperatures, for example about 10°–100° C, and pressures, of about 15–75 psi, are employed in a suitable, inert, liquid solvent, such as a lower alkyl alcohol of 1-6 carbon atoms, e.g. methanol, ethanol, isopropanol, n-butanol, and the like. Methanol is particularly effective. The catalyst may be any suitable platinum metal catalyst which is generally effective for hydrogenating a furoxan ring; especially effective is a palladium catalyst. The catalyst may be supported or unsupported, but preferably is supported on a carbon support. It appears that the hydrogenation medium should be slightly acidic to nullify any inhibitory effects which may occur due to amine intermediates. A trace amount of perchloric acid has been found to be particularly effective. The reduced product is then acylated with an acylating agent such as a suitable carboxylic acid of 1-4 carbon atoms or derivatives such as an acid chloride or anhydride, and may be substituted with 0-3 halogenatoms and preferably is an acetic acid or derivative such as the acylating agent trifluoroacetic anhydride.

Alternatively, the furoxan ring is reduced by reactively contacting the compound prepared in the previous step with a suitable reagent, e.g. a freshly activated zinc powder or, preferably, a zinc-silver couple, which is sufficient for furoxan reduction. Freshly activated zinc may be readily prepared by treating zinc dust with 10% hydrochloric acid over a short period of time with concentrated hydrochloric acid being added to maintain a vigorous evolution of hydrogen. The resulting solid is subsequently washed with water, acetone, ether, and hot acetic acid. The zinc-silver couple is prepared by thereafter treating the activated zinc with hot glacial acetic acid containing silver acetate for a short period of time. The resulting dark catalyst may be washed with dry methoxyethane to yield a suitable zinc-silver couple.

Preferably, in the reduction using activated zinc or the zinc-silver couple, the novel furoxan from step (f) is treated to simultaneously reduce the furoxan and acylate the amine moieties of the resulting reduced thiophene ring. This may be accomplished by placing the furoxan in trifluoroacetic anhydride and optionally a suitable inert, oxygenated hydrocarbon solvent such as dimethoxyethane and placing the solution in reactive contact with the activated zinc or zinc-silver couple. The mixture is kept in constant motion by stirring and the reaction takes place at low temperatures of about −5° to +10° C, preferably about 0° to 5° C over a period of time of about 2 hours preferably less than an hour and a half. The resulting reaction product can be recovered from the reaction mixture by usual recovery methods and separated, for example, on a silica gel column using chloroform as an eluent. The resulting compounds, 2(4-carbo lower alkoxy-butyl)-3,4-bis(alkamido)-2,5-dihydrothiophene are novel, either as a mixture of the dl-isomers or either isomer alone as, is this particular step for the preparation of the novel compounds.

h. Formation of dl-cis-2-(4-carbo lower alkoxy-butyl)-3,4-cis-bis(alkamido)-tetrahydrothiophene The novel dihydrothiophene from the previous step is hydrogenated using a suitable hydrogenation catalyst to form the novel compound of this step. The resulting hydrogenation products are novel compounds heretofore unknow in the art and the process for preparing said compounds is also novel. The hydrogenation is carried out in a suitable solvent using a hydrogenation catalyst suitable for effecting the selective hydrogenation of the thiophene ring. A particularly valuable catalyst is a palladium hydroxide catalyst which is approximately 20% palladium on G-60-charcoal, prepared according to a process described by M. Pearlman, *Tetrahedron Letters*, 1967, 1663. Preferably the catalyst is prehydrogenated. The hydrogenation is carried out in a suitable hydrogenating apparatus such as a Parr apparatus at suitable hydrogenating temperatures and pressures, for example a pressure of 50 to 70 pounds per square inch is usable and preferably 60 pounds per square inch is optimum. The temperature may be anywhere from 0 to 50° but preferably will be about room temperature, that is about 25° C. The reaction may take anywhere from 12 to 24 hours but preferably will be 24 hours or more to effect complete reaction. Preferably, the hydrogenation solvent is methanol. The cis-2(4-carbo lower alkoxy-butyl)-3,4-cis-bis (lower alkamido)-tetrahydrothiophenes are novel compounds either as mixtures of the dl-isomers or as the d- or l- isomer alone.

i. Formation of dl-biotin

The novel saturated thiophene from the previous step is converted to biotin by removing the acyl moieties and acylative cyclization of the resulting diamine. The 2 steps may be carried out without isolation of intermediates by treating the tetrahydrothiophene from the previous step with phosgene at low temperatures in a suitable solvent in the presence of a mild base. A suitable solvent may be a mixture of methanol and benzene, the methanol being substantially completely deoxygenated. The reaction mixture is stirred for several hours preferably no more than 2 and then is treated to recover the biotin.

j. Formation of d-biotin

The dl-biotin may then be resolved to obtain the d-biotin which is the active substance. This may be done by any method known in the art.

The following examples are given to illustrate the total synthesis of biotin as well as the synthesis of the unique intermediates in the preparation of biotin and the novel individual steps for preparing biotin intermediates. The examples are representative of the conditions under which biotin and the intermediates may be prepared but is not to be read in a limiting sense.

EXAMPLE 1

Preparation of Biotin

General Discussion of Experimental Parameters, Procedures, and Analysis

General Workup: In each step, the crude reaction product mixture was taken up in ethyl acetate, washed with aqueous solutions as indicated in the respective steps hereafter or saturated sodium chloride solution. The organic layer was dried over magnesium sulfate and evaporated using a laboratory rotary evaporator at the temperature indicated or at about 30° C.

Preparative column chromatography: As absorbent silica gel by Merck (particle size 0.05–0.2 mm) was used in 80-fold amount, and the solvents used are shown below where appropriate.

Thin Layer Chromatography (TLC): Analtech "Uniplate" precoated silica gel plates were used. Detection of the TL-spots was effected under UV-lamp and with ammonium molybdate-water-sulfuric acid solution (MOLLY) followed by heating the plate.

Crystallization were carried out from acetone-hexane or the solvents indicated in the steps hereinafter.

Melting points were obtained in open capillaries in an oil bath and are not corrected.

IR-spectra were run on a Perkin-Elmer 237 B Instrument from 2–3% substance/$CHCl_3$-solutions or specified conditions. The absorption bands are given in wave numbers (cm$^{-1}$).

The UV.-spectra were determined in ethanol solutions on a Carry Model 14 Recording Spectrophotometer. λ max.-terms are in nm and the intensities quoted as ε.

The mass spectras were recorded on Atlas CH-4 or CH-7 instruments.

The $^1$H-nmr-spectras were run on Varian instruments HA-100 (100MHZ) and Varian A-60(60MHZ). The chemical shifts given in δ-terms (ppm) with tertramethylsilane (TMS) as internal standard (=0). Abbreviations S=singlet, d=doublet, t=triplet, q=quadruplet, m=multiplet, b=broad single, J=coupling constant in HZ. The assigned number of protons comes from the electronically calculated integration and corresponds with the chemical structure.

The $^{13}$C-nmr-spectras were recorded on a Bruker C13 spectrometer 22.63MHZ.

PROCESS

In the following discussion the Roman numerals refer to the reaction scheme under "Summary of the Invention".

a. Forming Methyl-6-oxohexanoate (II-R=$CH_3$)

1.12 g (0.01 mol) methoxycyclohexene (I, prepared according to D.G. Linsay, Tet, 21, 1973 (1965),) were dissolved in 10 ml methanol, cooled to −78° C then ozonized for 30 min. The excess of ozone was removed with nitrogen. The ozonide in solution was treated with 800 mg dimethyl sulfide over a period of 15 min. at −78°. The solution was stirred for another 30 min. and then warmed up to room temperature. After stirring over night, the solvent was removed using a rotary evaporator (bath temperature below 40°). Distillation of the reaction mixture yielded 912 mg (63%) of methyl-6-oxohexanoate (II) as an oil, b.p. 60° (0.1mm).

ir ($CCl_4$): 2970, 2820, 2720, 1740, 1730.

nmr (A-60): 1.5–1.8, m, $CH_2$ (3&4); 2.2–2.6, m, $CH_2$ (2&5); 3.66, S, $COOCH_3$; 9.7, m, CHO.

$^{13}$C-nmr: 21.5, C (4); 24.3, C (3); 33.6, C (2); 43.4, C (5); 51.4, $OCH_3$, 173.1, C (6); 201.4, C (1).

ms m/e 145 ($M^{30}$+H); 116 (M+—CO); 113 (M+—$OCH_3$); 101 (M+—$CHOCH_2$); 87; 74.

b. Forming methyl-7-nitro-6-hydroxy-heptanoate (III-R=$CH_3$)

To a solution of 15.3 g nitromethane and 240 mg sodium hydroxide in 350 ml methanol a solution of 28.8 g aldehydoester II in 150 ml methanol was added at 0° C with vigorous stirring. The stirring was continued for 30 min. at 0° C. The reaction mixture was allowed to warm up to room temperature and another 5 ml nitromethane was added and the mixture stirred overnight at room temperature. General workup as discussed above yielded 36.6 g (89%) of methyl-7-nitro-6-hydroxy-heptanoate (III) as a yellow oil (mixture of two isomers).

nmr: 1.3–1.8, m, $CH_2$(3, 4&5); 2.2–2.5, m, $CH_2$ (2); 3.68, S, $COOCH_3$, 4.4, m, —$CH_2$—$NO_2$.

c. Forming methyl-7-nitro-6-acetoxy-heptanoate (IV-R=$CH_3$; $R^1$=$CH_3$

The crude mixture of isomers from b (III) was taken up in 280 ml acetic anhydride. 1.0 ml conc. $H_2SO_4$ was added and the reaction mixture was stirred overnight at room temperature. After removal of acetic anhydride at reduced pressure, the reaction mixture was treated according to the general workup, yielding 43.7 g (99%) of a crude brown oil consisting of the isomers of methyl-7-nitro-6-acetoxy-heptanoate (IV).

d. Forming the methyl ester of 7-nitro-hept-6-enoic acid (V-R=$CH_3$)

22 g crude nitroacetate (IV) were dissolved in 400 ml ethyl acetate and 11 g sodium bicarbonate and 20 drops water were added. The mixture was stirred 4 hours at 50° under nitrogen. The solution was filtered; the residue washed with ethyl acetate, dissolved in water and extracted with ethyl acetate. The combined organic layers were washed with water, dried and evaporated. After column chromatography with chloroform on silicagel, 6.3 g (38%) of the methyl ester of 7-nitro-hept-6-enoic acid (V) was collected (33% referred to II).

ir: 1735, 1645, 1520, 1345.-uv (εtoh) max 265 nm (8700).- nmr: 1.4–1.7, m,. $CH_2$ (3&4); 2.1–2.4, m, $CH_2$ (2&5); 2.68, s, $COOCH_3$; 6.8–7.6, CH (6&7).-

$^{13}$C-nmr: 24.3, C (3); 27.2 & 28.1, C (4&5); 33.5, C (2); 51.6, $OCH_3$; 140.0 & 142.1, C (6&7); 173.7, C (1).

Calculated for $C_8H_{13}NO_4$: C..51.33%; H..7.00%; N..7.48% Found for V: C..51.21%; H..7.02%; N..7.16% e. Forming the methyl ester of dl-7-thia-6-nitromethyl-9-nitro-nonanoic acid (VI-R=$CH_3$)

4.0 g nitroethyl thiol (prepared according to Example 2) were dissolved in 8 ml methanol, the ester (V) from the preceeding step in 8 ml methanol was added, and the mixture was stirred under $N_2$ for 2 hours at room temperature. General workup gave 7.5 g (80%) dl-7-thia-6-nitromethyl-9-nitro-nonanoic acid methylester (VI) as a yellow oil.

ir: 1725, 1550, 1435.

ms: 263 (M+—$CH_3O$); 248 (M+—$NO_2$)

Calc. for $C_{10}H_{18}N_2O_6S$: C..40.81%; H6.17%, N9.52% Found for $C_{10}H_{18}N_2O_6S$: C..40.73%; H6.23%; N9.47% f. Forming dl-6(4-carbomethoxy-butyl)-4H-6H-thieno[3,4-d]furoxan (VII-R=CH$_3$; R$^2$=CF$_3$)

12.4 g phosphorus oxychloride (POCl$_3$) were dissolved in 400 ml chloroform (dried over molecular sieve) and 20.1 g triethylamine (freshly distilled over LiAlH$_4$) were added. The mixture was allowed to cool to room temperature and 2.94 g of the ester VI from step $f$ in 200 ml dry CHCl$_3$ were added over a period of 18 hours at room temperature under N$_2$. The mixture was stirred an additional 1½ hours at room temperature. The black reaction mixture was poured on ice containing 5 ml conc. HCL, the layers separated, and the water phase washed three times with chloroform. The combined chloroform layers were washed with a small portion of saturated NaCl-solution, dried and evaporated using a rotary evaporator (water bath below 40° C). The black tar was chromatographed over a short column (20 g silicagel) with ether: hexane (2:1) as eluant yielding 2.1 g (81%) of the two isomeric furoxans (VII).
uv: 234, 265 nm (1750, 5130);
ir 1735, 1645, 1455, 980;
nmr: 1.5–1.8, n, CH$_2$ (3, 4&5); 2.2–2.4, m, CH$_2$ (2); 3.66, s, OCH$_3$; 3.9, d, CH$_2$(9), gem=12H. 4.4, b, CH (6);
$^{13}$C-nmr: shows two isomeric compounds
ms: 242 (M+—O), 227 (M+—OCH$_3$).
Calculated for C$_{10}$H$_{14}$N$_2$O$_4$S: C-46.50% H-5.46% N-10.85%
Found for C$_{10}$H$_{14}$N$_2$O$_4$S: C-46.56%; H-5.77%; N-10.53% g. Forming dl-2 (4 carbomethoxy-butyl)-3,4-bis-(trifluoroacetamido)-2,5-dihydro-thiophene (VIII-R=CH$_3$; R$^2$=CF$_3$)

Preparing a zinc-silver catalyst 17 g zinc dust (analytical grade) were treated with 100 ml 10% HCl and conc. HCL added to maintain a vigorous evolution of hydrogen over 10 minutes. The remaining solid was subsequently washed with two 100 ml portions of water, two 100 ml portions acetone, and two 100 ml portions ether, followed by washing with 100 ml glacial acetic acid (hot, warmed on the steam bath for 15 min). A second 100 ml hot glac. acetic acid containing 200 mg silver acetate (analytical grade) was added. The mixture was vigorously shaken for 1 minute, the dark catalyst then washed with 2 × 100 ml dry dimethoxyethane (DME), yielding a zinc/silver catalyst sufficient for furoxan reduction. Proof of the activity of the catalyst was evident due to a rise of temperature as the furoxan/DME/(CF$_3$CO)$_2$O mixture was added.

Reduction of Furoxan and reaction with trifluoroacetic acid 2.5 g of the furoxan (VII) in 16 ml dry dimethoxyethane and 16 ml trifluoroacetic anhydride were added to the catalyst (prepared from 17 g Zn-dust as discussed above) in 20 ml dimethoxyethane at 5° C over 75 minutes. The stirring was continued for 10 minutes. General workup gave 1.980 g of a yellow oil containing impurities (complex GLC). Separation on 300 g silica gel with chloroform containing 1% MeOH yielded 1.59 g of the pure dihydrothiophene (VIII) (38%) as white needles; mp 84°–85° (ether).
ir: 3250, 1735, 1710, 1170, 880;
nmr: 1.4–1.8, m, CH$_2$ (3,4&5); 2.25–2.45, m, CH$_2$ (2); 3.65, S, OCH$_3$; 3.85, m, CH (a), 4.1, m, CH (9); 4, 4, b, CH (6);

$^{13}$C-nmr: 24.12, C (3); 25.45, C (5); 32.74, C (4); 33.81, C (2) 34.92, C (9); 48.60, C (6); 51.79, OCH$_3$; 109.26 & 121.98, CF$_3$; 124.12, C (8); 125.3, C (7); 174.84, C (1).
ms: 422 (M+), 391 (M+—OCH$_3$), 309 (M+—NH$_2$·COCF$_3$), 307 (M+— side chain).
Calculated for C$_{14}$H$_{61}$N$_2$O$_4$F$_6$S: C, 39.81%; H, 3.82% N, 6.63%.
Found for C$_{14}$H$_{16}$N$_2$O$_4$F$_6$S: C, 40.02% H, 3.96%, N, 6.77%.

h. Forming dl-cis-2 (4-carbomethoxy-butyl)-3,4-cis-bis (trifluoroacetamido)-tetrahydrohiophene (IX-R=CH$_3$; R$^2$=CF$_3$)

120 mg of the dihydrothiophene (VIII) were dissolved in 2 ml MeOH and added to a suspension of 120 mg prehydrogenated (1 hour, 60 psi) Pd (OH)$_2$-catalyst (ca.20% Pd on DarcoG-60-charcoal, prepared according to M. Pearlman, Tetrahedron Letters, 1967, 1663.) in 2 ml MeOH. The hydrogenation was carried out in a Parr-apparatus with a small bottle, at 60 psi H$_2$ and room temperature, over 24 hours. The catalyst was filtered off and washed with methylene chloride. The solvent was evaporated yielding 84 mg. of the tetrahydrothiophene (IX) as an oil which decomposed during all purificication attempts, and was thus used directly for the next step.
gc-ms: 393 (M+—OCH$_3$), 311 (M+-NH$_2$COCF$_3$), 197 (M+—2NH$_2$COCF$_3$), 166 (M+—2NH$_2$COCF$_3$—OCH$_3$).

i. Forming dl-biotin (X)

The 84 mg hydrogenation product (IX) were dissolved in 10 ml deoxygenated methanol and 1 g K$_2$CO$_3$ in 10 ml H$_2$O was added. The reaction mixture was stirred overnight at room temperature under N$_2$. Then 40 ml phosgene (12.5%) in benzene was added to the precooled (0°) mixture. After stirring for 2 hours at room temperature the reaction was taken up in ethyl acetate and 10% acetic acid, washed with a small amount of ice water and filtered with about 1 g Darco G-60 to remove the yellow color. The charcoal was well washed and then eluted with 5 ml 5 N ammonium hydroxide. The solvents were evaporated and the product mixture chromatographed on silica gel with ethyl acetate and 5% acetic acid yielding 53 mg of dl-biotin (X) which, after recrystallization from 5 N ammonium hydroxide (solution and reacidification) melted at 224°;
ir: 3350, 3250, 3060, 1705, 1660, 1250, 1180;
nmr: 1.25–1.70, m, CH$_2$ (3, 4&5); 2.10–2.30, m, CH$_2$, m, CH$_2$ (2); 2.6, D, CH (9$\beta$); J$a\beta$,ax=12 HZ; 2.85, dd, CH (9x), ---- J$_{9a,8}$=5HZ; 3.1–3.2, m, CH (6); 4.1–4.4, m, CH (7&8); 5.3–5.5, b, NH (2H).-$^{13}$C
nmr (DMSO): 24.48, C (3); 28.02, C (4&5);33.45, C (2); 39.53, C (9); 55.33, C (6); 5 g.20, C (8); 61.05, C (7); 162.77, N$_2$C=O; 174.45, C (1).
ms: 244 (M+); 184 (M+—CH$_2$COOH-H); 112;97 (base peak); 85; identical with authentic d-biotin ms.

j. Resolution of dl-biotin

A mixture of 7 mg dl-biotin (14) and 7 mg (ca. 10% excess) of L (+)-arginine was dissolved in 1 ml H$_2$O and the solution was diluted with isopropyl alcohol. The solution was cooled to 0° C and kept in the refrigerator overnight. The crystals were filtered and washed with acetone yielding 6.5 mg. The L (+)-arginine salt of dl-biotin was dissolved in 1 ml H$_2$O and acifified with 1N HCL. The crystalline d-biotin was filtered, washed with cold water and dried in vacuo yielding 1.8 mg of d-biotin (27% ) m.p. 228°–229° C. A mixed m.p. with d-biotin gave no depression in m.p.

EXAMPLE 2

Preparation of Nitroethanethiol

This example shows a particularly preferred method of preparing nitroethanethiol which is used in step (e), above. 80 g dry paraformaldehyde were suspended in 1.6 l nitromethane ($CH_3NO_2$). After addition of 3 ml of 3 N potassium hydroxide (KOH) in methanol the suspension was stirred for 30 min. The now clear solution was acidified with 1.5 ml conc. sulfuric acid, stirred for an additional 30 min and filtered. The excess $CH_3NO_2$ was distilled off at 30°–50° C bath temperature and the residue distilled at about 1 mm/50° C yielding 106 g colorless nitroethanol.

64 g nitroethanol, 50 ml glacial acetic acid, 250 ml benzene and 5 drops conc. $H_2SO_4$ were refluxed, using a water separator for 8 hours; 12 ml of $H_2O$ were collected. The solution was evaporated and vacuum distilled (1mm at 60° C) yielding 89 g colorless nitroethylacetate.

80 g sodium hydroxide were dissolved in 500 ml water and 35 ml phosphorous thiochloride ($PSCl_3$—98%) were added to maintain the reaction temperature between 75° and 85° C (ca. 30 min). The reaction was stirred at 80° C until all the $PSCL_3$ had reacted (45 min). Then the reaction mixture was put into the refrigerator (0° C) over night. The precipitated white crystals were filtered off and washed with 100 ml EtOH. The crystals were dissolved in 250 ml distilled water at 45° C and reprecipitated by the slow addition of 200 ml ethanol (EtOH) under rapid stirring. The solution was cooled to room temperature, filtered, and the collected white crystals were washed with 100 ml EtOH.

The resulting product was dehydrated by stirring in 600 ml absolute MeOH for 1½ hours. The fine white powder was filtered off and dried at 105° C (vacuum) for 1 hour yielding 38 g (59%) of anhydrous trisodium thiophosphate ($Na_3PO_3S$). To a solution of 54.3 g $Na_3PO_3S$ in 600 ml dist. water were added 0.5 g benzyltriethylammonium chloride, the mixture cooled to 15° and then 39.9 g nitroethyl acetate, prepared above, was added during 15 min, the temperature being maintained below 20° C. The mixture was stirred at room temperature for 16 hours, then acidified with 60 ml conc. HCl and hydrolyzed at 40° for 1 hour. After a work up according to the general procedure in Example I, the residue was distilled yielding 9.7 g (30%) nitroethanethiol b.p. 37°–39° (0.3 mm).

We claim as our invention:

1. The process of preparing biotin which comprises
   a. ozonizing a lower alkoxycyclohexene to form the lower alkyl ester of 6-oxohexanoic acid;
   b. reacting nitromethane with the lower alkyl ester of 6-oxo-hexanoic acid from step (a) under basic conditions in the presence of a solvent suitable for nitromethylation to form the lower alkyl ester of 7-nitro-6-hydroxy-heptanoic acid;
   c. reacting the product of step (b) with a lower alkanoic acid or its halide or anhydride derivative to form the lower alkyl ester of 7-nitro-6-lower alkanoyl -heptanoic acid;
   d. placing the reaction product of step (c) in a suitable solvent under basic conditions at slightly raised temperatures to form the lower alkyl ester of 7-nitrohept-6-enoic acid;
   e. reacting nitroethanethiol with the reaction product from step (d) in an inert atmosphere, in a solvent and under conditions suitable for nucleophilic addition to form the lower alkyl ester of dl-7-thio-6-nitromethyl-9-nitrononanoic acid;
   f. reactively contacting the reaction product of step (e) with a catalytic amount of a tertiary alkyl amine and phosphorus oxychloride under substantial anhydrous conditions in a substantially inert atmosphere in a suitable solvent to form dl-6-(4-carbo lower alkoxy-butyl)-4H-6H-thieno [3,4-d]-furoxan;
   g. reducing the product from step (f) by catalytic hydrogenation or by using a suitable reducing agent and acylating with a suitable carboxylic acid of one to four carbon atoms or its acid chloride or anhydride derivative, said acid or its derivative being substituted with from 0 to 3 halogens, to form dl-2(4-carbo lower alkoxy-butyl)-3,4-bis(alkamido)-2,5-dihydro-thiophene;
   h. selectively hydrogenating the product from step (g) to form dl-cis-2(4-carbo lower alkoxy-butyl)-3,4-cis-bis(alkamido)-tertrahydro-thiophene;
   i. hydrolyzing and cyclizing the product from step (h) to form dl-biotin.

2. The process of claim 1 wherein said dl-biotin is resolved to form d biotin.

3. The process of claim 1 wherein said lower alkoxyclohexene is methoxycyclohexene and said acylating agent in step g is trifluoroacetic anhydride.

* * * * *